(12) United States Patent
Rueckert et al.

(10) Patent No.: US 9,074,240 B2
(45) Date of Patent: Jul. 7, 2015

(54) SYMMETRICAL TEST ELEMENT FOR DETECTING AN ANALYTE

(71) Applicant: Roche Diagnostics Operations, Inc., Indianapolis, IN (US)

(72) Inventors: Frank Rueckert, Ludwigshafen (DE); Bruno Thoes, Kaiserslautern (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 14/284,598

(22) Filed: May 22, 2014

(65) Prior Publication Data

US 2014/0255962 A1   Sep. 11, 2014

Related U.S. Application Data

(63) Continuation of application No. PCT/EP2012/073221, filed on Nov. 21, 2012.

(30) Foreign Application Priority Data

Nov. 24, 2011   (EP) .................................... 11190608

(51) Int. Cl.
*C12Q 1/54* (2006.01)
*G01N 33/66* (2006.01)
(Continued)

(52) U.S. Cl.
CPC ......... *C12Q 1/54* (2013.01); *Y10T 436/144444* (2015.01); *G01N 27/3271* (2013.01); *G01N33/4875* (2013.01); *C12Q 1/26* (2013.01); *C12Q 1/32* (2013.01); *G01N 27/416* (2013.01); *G01N 33/66* (2013.01)

(58) Field of Classification Search
CPC .............. C12Q 1/26; C12Q 1/32; C12Q 1/54; G01N 27/3271; G01N 27/416; G01N 33/48; G01N 33/4875; G01N 33/66; Y10T 436/144444; Y10T 436/2575

USPC ............ 436/63, 95, 164, 165, 169, 170, 180; 422/400, 420, 421, 82.05, 82.09; 435/14, 29, 25, 26
See application file for complete search history.

(56) References Cited

U.S. PATENT DOCUMENTS

2002/0192807 A1 * 12/2002 Haviland et al. ............ 435/287.2
2003/0169426 A1 *  9/2003 Peterson et al. ............... 356/446
(Continued)

FOREIGN PATENT DOCUMENTS

EP     0547710 A2   12/1992
EP     0302287 B1   12/1993
(Continued)

OTHER PUBLICATIONS

Hönes, Joachim et al., "The Technology Behind Glucose Meters: Test Strips," Diabetes Technology & Therapeutics, 2008, pp. S10-S26, vol. 10, Supplement 1.

*Primary Examiner* — Maureen Wallenhorst
(74) *Attorney, Agent, or Firm* — Roche Diabetes Care, Inc.

(57) ABSTRACT

Test elements are disclosed for detecting at least one analyte in a body fluid. The test element include at least one strip-shaped carrier element and at least one test field having at least one test chemistry for detecting the analyte. The test element has a symmetrical shape such that the test element may be inserted in one of at least two different correct measurement orientations into a test element receptacle of a testing device, which includes a detection device. In the different orientations, at least one analyte-induced change in the test chemistry of the test field is detectable. Test systems including the test elements and methods of detecting at least one analyte in the body fluid using the test elements also are disclosed.

19 Claims, 4 Drawing Sheets

(51) Int. Cl.
*G01N 27/327* (2006.01)
*G01N 33/487* (2006.01)
*C12Q 1/26* (2006.01)
*C12Q 1/32* (2006.01)
*G01N 27/416* (2006.01)

(56) References Cited

U.S. PATENT DOCUMENTS

2010/0270149 A1 10/2010 Wang et al.
2010/0331653 A1 12/2010 Stafford
2014/0174953 A1* 6/2014 Elder et al. .................. 205/782

FOREIGN PATENT DOCUMENTS

| EP | 0821234 A2 | 1/1998 |
| EP | 1593434 A2 | 11/2005 |
| WO | 2010/094426 A1 | 8/2010 |
| WO | 2010/094427 A3 | 8/2010 |

* cited by examiner

SYMMETRICAL TEST ELEMENT FOR DETECTING AN ANALYTE

CROSS-REFERENCE TO RELATED APPLICATIONS

This patent application is a continuation of Int'l Patent Application No. PCT/EP2012/073221; filed 21 Nov. 2012, which claims priority to and the benefit of EP Patent Application No. 11190608.7; filed 24 Nov. 2011. Each patent application is incorporated herein by reference as if set forth in its entirety.

TECHNICAL FIELD

This disclosure relates generally to chemistry, medical diagnostics and engineering, and more particularly, it relates to symmetrical test elements for detecting at least one analyte in a body fluid sample, where the symmetrical test elements have a plurality of correct measurement orientations when placed in a testing device.

BACKGROUND

In medical diagnostics, body fluid analysis is routinely performed to qualitatively and/or quantitatively detect one or more analytes therein. In view of the obtained analyte concentration, a physician then makes decisions regarding a potential treatment of the person from whom the body fluid sample was taken.

Typically, test elements are used for detecting an analyte of interest and can be in a form such as test strips that include one or more test fields having one or more test chemistries. The test chemistries are adapted to change one or more detectable properties in the presence of the analyte to be detected. Thus, electrochemically detectable properties of the test chemistry and/or optically detectable properties of the test chemistry may be changed due to the presence of the analyte. For potential test chemistries that may be used within the present disclosure, reference may be made to Hönes et al. (2008) *Diabetes Technol. Ther.* 10(Supp. 1):S10-S26; and Int'l Patent Application Publication Nos. WO 2010/094426 and WO 2010/094427. However, other types of test chemistries may be used within the present disclosure.

Many different types of test elements having test chemistries are known. For example, EP Patent Application Publication No. 0 302 287 describes a test element for detecting an analyte in blood by using reagents included in a test carrier. The test carrier includes a frame of a plastic material and a multi-layer test field mounted inside the frame.

EP Patent Application Publication No. 0 547 710 describes a cartridge-free stack of test elements. The test elements are not housed in a cartridge and are temporarily and non-destructively fused together so that the stack can be used without a need for a cartridge.

EP Patent Application Publication No. 1 593 434 describes a method of manufacturing an analytical band for liquid samples, specifically for body fluids. In the method, a multiplicity of test fields are manufactured in the form of test labels that then are glued to a transport tape.

EP Patent Application Publication No. 0 821 234 describes a diagnostic test element for determining an analyte concentration or presence in blood. The test element includes a reagent system including a color-forming reagent and a test field having a sample application side and a detection side. The test field is designed so that erythrocytes are prevented from reaching the detection side. The test element also can include a positioning hole to position the test strip inside a diagnostic testing device.

As with test elements, many testing devices are commercially available. A large number of testing devices and systems are known that use test elements in the form of test strips. For example, applications are known in which a multiplicity of test strips are provided by a magazine, where one test strip from the magazine automatically may be provided to the testing device. Other applications, however, are known in which single test strips are used and are inserted into the testing device manually by a user.

Typically, one end of the test strip is adapted to be inserted into the testing device and for detecting the analyte, while the opposing end of the test strip serves as a handle enabling the user to push the test strip into the testing device or to pull the test strip from the testing device.

For applying the sample to the test element, typical test elements therefore provide at least one sample application site, such as a capillary opening in capillary test elements or a sprite net in optical test elements having a top dosing system. Test elements of this type are commercially available, for example, under the trade name Accu-Chek® Active.

In such test elements, the opposing ends intentionally are designed asymmetrically so that the user may readily identify the end of the test element to be inserted into the testing device and a correct orientation for insertion. Typically, the test field is located closer to the front end of the test element, which is inserted into the testing device, whereas the longer end of the test element may be used as a "handle" to enable the user to push or pull it.

Unfortunately in the field of home monitoring performed by elderly persons, children or disabled persons, confusion about the orientation of the test strip often occurs. For example, the user unintentionally may introduce the long end of the test strip rather than the end having the test field into the testing device and/or may introduce the test element into the testing device with the backside facing in an upward direction. Consequently, each test element typically provides at least four different orientations, whereof three orientations are incorrect and only one orientation is a correct measurement orientation.

A test system is needed that is capable of detecting an incorrect insertion of the test element and, preferably, that brings the incorrectly inserted test element to the user's intention. These requirements, however, imply a significant technical effort with regard to testing devices for detecting the incorrect insertion and/or for processing the information regarding the incorrect insertion and for implementing appropriate process steps, such as an output of warnings to the user.

For the foregoing reasons, there is a need for improved test element designs that reduce the technical effort for detecting incorrect insertions of the test elements and, still, provide a high degree of protection against unintentional malfunctions of the test system due to an incorrect insertion of the test element.

BRIEF SUMMARY

This disclosure describes test elements, testing systems and methods of detecting an analyte in a body fluid sample. To address the disadvantages noted above, an inventive concept provided herein includes symmetrical test elements that may be inserted in at least two different, and correct, measurement orientations into a test element receptacle of a testing device, where regardless of the orientations, at least one analyte-induced change in the test chemistry of the test field is detectable. The inventive concept is embodied in exemplary test elements, testing systems and methods as described herein.

In one aspect, test elements are provided for detecting at least one analyte in a body fluid. The test elements include at least one strip-shaped carrier element and at least one test field having at least one test chemistry for detecting the at least one analyte, where the test elements are symmetrical (i.e., symmetrically shaped/symmetrically oriented).

In some instances, the test elements are test strips.

Test element having a symmetrical shape may include a sample test strip having two identical ends that may be introduced into a sample receptacle, such as a measurement opening, of a testing device. In any of the correct measurement orientations, the test field may be positioned in a measurement position, such as in a field of view of the detection device of the testing device. Accordingly, the test element may include two or more correct measurement orientations, in which the test element may be inserted into the test element receptacle and in which, the test field is correctly positioned with regard to the detection device. Thus, for example, for a test element formed as a test strip, having four potential orientations, in which the test strip may be inserted into the test element receptacle, the test element may be designed symmetrically such that two of the four orientations or even all four orientations may be correct measurement orientations allowing for a detection of the analyte.

In some instances, the test element may be designed as a symmetrical test strip having a top dosing system in which a sample application site is a surface of the test field, where two correct measurement orientations out of four generally possible orientations of insertion are given. In other instances, the test element may be designed as a capillary test element having fully symmetric properties in which all four of the possible insertion orientations are correct measurement orientations.

In another aspect, systems are provided for detecting an analyte in a body fluid with the test elements disclosed herein. The systems include at least one testing device and at least one test element as disclosed herein. The at least one testing device includes a test element receptacle and a detection device. In some instances, the testing device includes one or more evaluation devices or evaluation units, such as at least one evaluation device having at least one data processing device.

In view of the foregoing, methods are provided for detecting an analyte in a body fluid sample. The methods include a step of providing a test element as disclosed herein and a step of inserting the test element in a user-selected orientation into a testing device so that the test element is in one of the at least two correct measurement orientations. The methods also include a step of detecting at least one analyte-induced change in test chemistry of the test element and then providing a quantitative or qualitative analyte result based upon the analyte-induced change.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein:

FIGS. 1 A-B show different views of a test system for use with the test elements as disclosed herein.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The test elements, systems and methods now will be described more fully hereinafter with reference to the accompanying drawings, in which some, but not all embodiments of the inventive concept are shown. Indeed, the test elements, systems and methods may be embodied in many different forms and should not be construed as limited to the embodiments set forth herein; rather, these embodiments are provided so that this disclosure will satisfy applicable legal requirements.

Likewise, many modifications and other embodiments of the test elements, systems and methods described herein will come to mind to one of skill in the art to which the disclosure pertains having the benefit of the teachings presented in the foregoing descriptions and the associated drawings. Therefore, it is to be understood that the test elements, systems and methods are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the test elements, systems and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may both refer to a situation in which, besides B, no other element is present in A (i.e., a situation in which A solely and exclusively consists of B) or to a situation in which, besides B, one or more further elements are present in A, such as element C, elements C and D, or even further elements.

Overview

Exemplary test elements, systems and methods are provided and are based upon the inventive concept of symmetrically shaped test elements having at least two or more correct measurement orientations.

As used herein, "symmetrical shape" or "symmetrically shaped" means a design of a test element so that more than one orientation exists in which the test element may be inserted into a test element receptacle of a testing device so that the detection device may detect changes in the test chemistry of the test field. Thus, the symmetrical shape may be such that, in at least two orientations, in each case, the test field is located in the field of view of an detector of the detection device, such as in front of an optical detection window of an optical detector of the detection device, independent from the choice of the orientation of the test element. The symmetrical shape therefore provides at least two correct measurement orientations of the test element.

As used herein, "test element" means an arbitrary device such as an arbitrary monolithic device or one-piece device, which is capable of detecting an analyte in a body fluid sample. The test element typically includes at least one component, such as a test chemistry or test chemistries, that changes at least one detectable property when exposed to the analyte that is present in the body fluid. The test chemistry may be designed to change at least one optical property (e.g., color) and/or to change at least one electrochemically detectable property when the analyte is present. Analyte detection may be specific and may be a qualitative and/or a quantitative detection.

As used herein, "orientation" means an arbitrary alignment in a given coordinate system, in which the test element may be inserted into the test element receptacle of the testing device, where the test element receptacle is in a fixed position and alignment in the coordinate system. Thus, the test element may have at least two opposing ends, such as edges along opposing broad sides of the test element that may function as leading edges when inserting the test element into the test element receptacle, where in both cases, the test element is positioned in the test element receptacle such that the at least one detection device may detect the at least one analyte-induced change in the test chemistry of the test field of the test element.

The test elements, systems and methods disclosed herein imply a large number of advantages over known test elements, systems and methods. For example, the test elements, systems and methods provide a high degree of user friendliness, since the degree of attention the user has to pay during insertion of the test element into the test element receptacle is significantly decreased by providing a larger number of correct measurement orientations of the test element. Similarly, the test system provides a higher degree of sale-safety than conventional systems when used by handicapped users or children, as the danger of choosing an inappropriate and incorrect measurement orientation of insertion of the test element is significantly reduced.

Further, this disclosure provides the advantage that, from a design perspective, only minor amendments with regard to conventional test elements such as conventional asymmetric test strips are required. Thus, the solution disclosed herein may be readily implemented into existing test systems. In fact, known testing devices may still be used and a redesign only for the test element may be required. Moreover, the solution described herein may readily and cost-effectively be implemented even into existing systems. The present inventive concept therefore provides test elements, systems and methods of detecting an analyte of interest in a body fluid sample, where the test elements can be inserted into a testing device in two or more correct measurement orientations.

Test Elements

Test elements incorporating the inventive concept are provided herein. Such test elements include at least one carrier element and at least one test field having at least one test chemistry for detecting an analyte of interest in a body fluid sample.

As used herein, "carrier element" means an arbitrary element comprising one or more components, where the carrier element may be handled as one piece and where the carrier element is adapted to carry other components of the test element such as, for example, at least one test field. Thus, the carrier element may have a single-layer set-up or a multi-layer set-up, such as a laminate set-up. The carrier element may include one or more materials such as plastic materials, paper materials, cardboard materials and/or ceramic materials. In some instances, the carrier element is one or more plastic materials. Examples of plastic materials include, but are not limited to, polycarbonate, polyethylene, polyethylene terephthalate and acrylonitrile-butadiene-styrene. Additionally or alternatively, other plastic materials can be used. The carrier element also can include one or more metallic materials such as aluminum. Further, combinations of materials are possible, such as laminate materials, where the combinations are of two or more different types of materials, such as a combination of plastic materials and metallic materials in a layer setup.

As used herein, "test field" means any contiguous and/or continuous amount of test chemistry having an arbitrary geometric shape. In some instances, the test field may include one or more layers of test chemistry and/or other materials, such as one or more layers having a thickness below about 1 mm, or from about 10 µm to about 800 µm, or even from about 50 µm to about 600 µm. Thus, the test field may include one or more layers of the at least one test chemistry and, optionally, one or more additional layers such as one or more layers of reflective pigments such as $TiO_2$-pigments. Alternatively or additionally, the test field may include one or more spreading layers, such as one or more sprite layers, such as sprite nets, which are designed to spread the sample over an optional sample application surface of the test field.

As used herein, "test chemistry" means an arbitrary material or a composition of materials adapted to change at least one detectable property in the presence of the at least one analyte (i.e., at least one analyte-induced change). This property may be an electrochemically detectable property and/or an optically detectable property, such as a color change and/or a change in remissive properties. Chemistries or electrochemically and/or optically detecting analytes are well-known in the art and are referenced elsewhere herein. Regardless, the at least one test chemistry may be a highly selective test chemistry, which only changes the property if the analyte is present in a sample of a body fluid applied to the test element, whereas no change occurs if the analyte is not present. In some instances, the degree or change of the at least one property is dependent on the concentration of the analyte in the body fluid to allow for a quantitative detection of the analyte. For example, the test chemistry may include at least one enzyme, such as glucose oxidase and/or glucose dehydrogenase. Additionally or alternatively, the test chemistry may include one or more co-enzymes and/or one or more mediators. Alternatively or additionally still, the test chemistry may include one or more dyes, which in interaction with the one or more enzymes, may change color in the presence of the at least one analyte to be detected.

The at least one analyte-induced change in the test chemistry therefore can be an electrochemically, electronically and/or optically detectable change. In some instances, the analyte-induced change in the test chemistry is an optical change such as a color change and/or a change in a remission, where the optical change may be detected by using an optical detector of a detection device.

In some instances, the test elements are strip-shaped and thus known as test strips. As used herein, "strip-shaped" mean a test element having an elongated shape and a thickness, where an extension of the test element in a lateral dimension exceeds the thickness of the test element, such as by at least a factor of about 2, by at least a factor of about 5, by at least a factor of about 10, by at least a factor of about 20, or by at least a factor of about 30. Thus, a strip-shaped test element may have a thickness below about 3 mm, below about 2 mm, or even below about 1 mm.

As used herein, "about" means within a statistically meaningful range of a value or values such as a stated concentration, length, molecular weight, pH, sequence identity, thickness, time frame, temperature, volume or width. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

When the test element is a test strip, the carrier element likewise may be strip-shaped and may have a rectangular shape, with a broad side and a longitudinal side and a thickness, where the length of the broad side is smaller than the length of the longitudinal side by at least a factor of about two. In some instances, the broad side may have a length of about 1 mm to about 20 mm or of about 3 mm to about 10 mm. The longitudinal side may have a length of about 10 mm to about 100 mm or of about 20 mm to about 70 mm. With regard to potential thicknesses of the carrier element, reference may be made to the above-mentioned thicknesses. In other instances, the strip-shaped carrier element has an elongate rectangular form.

As used herein, "elongate" means rectangular form having a longitudinal side and a broad side, where the length of the longitudinal side exceeds the length of the broad side by at least a factor of about 1.5, by at least a factor of about 2, or by at least a factor of about 4.

As part of the inventive concept, the test elements disclosed herein have a symmetrical shape so that the test element may be inserted in at least two different, correct measurement orientations into a test element receptacle of a testing device having a detection device, where in the different orientations, at least one analyte-induced change in the test chemistry of the test field is detectable. The orientation in which at least one analyte-induced change in the test chemistry of the test field is detectable by the testing device is referred to as a "correct measurement orientation." Other orientations of the test element, even though an insertion into the test element into the test element receptacle may be possible, which do not allow for a detection of the analyte-induced change in the test chemistry, such as due to a misalignment of the test field and a detector of the testing device, are referred to as "incorrect orientations." Stated differently, the test elements disclosed herein have a symmetrical shape so that the test element may be inserted in at least two correct measurement orientations into the test element receptacle of the testing device.

The test elements thus may have a symmetry such as a two-fold symmetry or a four-fold symmetry. As used herein, "symmetry" means a mirror symmetry about a virtual line, a virtual plane, and/or may mean a rotational symmetry about a virtual axis of rotation. As used herein, "two-fold symmetry" means that the test element may be transformed by a symmetry transformation, such as a mirroring about the line or plane mentioned above and/or a rotation about the rotational axis mentioned above, thereby transforming the test element into a test element having at least essentially the same shape as before performing the symmetry transformation by repeating the transformation, the test element returns to its original shape. Correspondingly, "four-fold symmetry" means a three-fold repetition of the first transformation transforms the test element into its original orientation.

Generally, and as mentioned above, the symmetry may be a mirror symmetry about a virtual middle plane of the test element such as a middle plane perpendicular to a plane of the strip-shaped carrier element; or a symmetry with respect to a virtual line or axis such as a symmetry axis centrally penetrating the test element. Thus, the test element may be mirror-symmetric with respect to a middle plain perpendicular to a plane of extension of the carrier element. This mirror plane may symmetrically divide the longitudinal side of the elongate rectangular form into two halves, where by the virtual middle plane, the test element may be divided into two identical halves. When the test element has a carrier element having a rectangular shape, the test field may be located such that a distance between the test field and a first broad side or edge of the carrier element substantially is the same as a distance between the test field and a second broad side or edge of the carrier element, where the first broad side and the second broad side are located at opposing ends of the rectangular carrier element.

As used herein, "substantially" means that deviations by no more than about 2 mm may be tolerated, by no more than about 1 mm, or by no more than about 500 µm.

In some instances, the test elements may be a single-use test strip. As used herein, "single-use test strip" means an element designed to be used only once for detecting the analyte in a sample of the body fluid. Thus, the test element may include a test field that irreversibly changes one or more properties when a sample containing the analyte is applied to the test field so that further tests may not be performed with the test field. The single-use test strip typically includes one test field.

As noted herein, the test element receptacle of the testing device is adapted to mechanically interact with the test element. As such, the test element and even the carrier element of the test element may include at least one mechanical positioning aid, where the positioning aid engages, in each of the at least two different orientations, at least one positioning element of the testing device to position the test field in all orientations in a substantially identical position with regard to the detection device.

As used herein, the term "substantially identical position" refers to an identical position, where positioning tolerances of no more than about 1 mm in each dimension or of no more than about 500 μm may be tolerated.

As used herein, "mechanical positioning aid," "positioning aid" and "positioning element," respectively, each means one or more mechanical elements that may interact to provide a mechanical positioning of the test element such as a mechanical fixation of the test element. Thus, the positioning aid and the positioning element may interact by using a key-hole-principle and/or by any other mechanical engagement mechanism.

In some instances, the positioning aid may be at least one notch positioned at a longitudinal side of the carrier element, at least two notches positioned at opposing longitudinal sides of the carrier element; at least two notches positioned symmetrically with regard to the test field, such as at least two notches located at opposing longitudinal sides of a carrier element of the test element; at least one cavity or hole in the carrier element; at least one through-hole; at least two cavities or holes; at least two cavities or holes positioned symmetrically with regard to the test field; at least one catch profile adapted to engage at least one catch element of the positioning element; or at least two catch profiles positioned symmetrically with regard to the test field. Generally, the mechanical positioning aid of the test element may be at least two mechanical positioning aids positioned symmetrically with regard to the test field, with regard to one or more of the above-mentioned symmetry transformations.

The test elements also may include at least one orientation indication element. As used herein, "orientation indication element" means an element that may be detected by at least one orientation detector of the testing device and that is adapted to indicate to the orientation detector a correct positioning of the test element. The orientation indication element may include one or more orientation indication elements. In some instances, the orientation indication element has a symmetrical shape, such that the orientation indication element may be detected by at least one orientation detector of the testing device when the test element is inserted into the test element receptacle in the orientations. Likewise, the orientation indication element may include at least one color field, such as a black field, that may be positioned on a backside of the carrier element opposing the test field. In some instances, the color field may include at least two color fields such as at least two black fields positioned symmetrically with regard to the test field.

The test elements also may include at least one sample application site. As used herein, "sample application site" means an arbitrary site adapted so that a sample of the body fluid may be applied to the test element at the sample application site by a user. Sample application may take place in a state in which the test element is separated from the testing device (so-called outside mode) and/or in a state in which the test element is inserted into the test element receptacle (so-called inside mode) of the testing device. The symmetrical shape of the test element may be such that, in all correct insertion orientations of the test element into the test element receptacle, a sample application may be possible. Examples of sample application sites include, but are not limited to, an opening of at least one capillary element leading from the sample application site to the test field; a sample application surface of the test field, such as a surface of the test chemistry; and/or an application surface having at least one spreading element such as a spreading net.

In some instances, the test elements may include at least two sample application sites, where the sample application sites may be located symmetrically with regard to the test field. Thus, one test field may be provided, where a sample may be applied to at least two different sample application sites, and where after application to one or more of these sample application sites, the sample is guided to one and the same test field.

The test elements also may include one or more capillary elements. As used herein, "capillary element" means an element adapted to transport the sample of the body fluid by capillary forces. The capillary element may include one or more capillary caps, one or more capillary slots, and/or one or more capillary tubes having an arbitrary cross-section, such as a round cross-section and/or a polygonal cross-section. In some instances, the test element may include at least two capillary elements located symmetrically with regard to the test field, where the capillary elements convey the sample from at least one opening of each capillary element to the test field.

In some instances, and in the context of test elements having one or more capillary elements, the test field may include at least two viewing fields on opposing sides of the test element. As used herein, "viewing field" means a surface visible from the outside of the test element and through which the analyte-induced change in the test chemistry of the test field may be detected by optical detection methods. In some instances, the test field may include at least two viewing fields on opposing sides of the test element for detecting an optical change of the test chemistry, such as a color change of the test chemistry. Thus, the test field may include test chemistry on both sides of the test element and/or in the interior of the test element, where the test chemistry is visible from both sides.

Systems

In view of the test elements above, systems that use the test elements are provided herein that incorporate the inventive concept. Such systems include at least one testing device and at least one test element as disclosed herein.

As used herein, "testing device" means an arbitrary device such as an electronic and/or optoelectronic device, which may be handled independently from the test element(s). The testing device, however, is adapted to interact with test elements through a test element receptacle to thereby detect the at least one analyte-induced change in the at least one property of the test chemistry such as, for example, an optical change. The testing device also is adapted to derive at least one information regarding the presence and/or concentration of the analyte in the body fluid from detecting the at least one change in the test chemistry. Thus, the testing device may include at least one electronic evaluation device interacting with at least one detection device to derive the at least one information regarding the presence and/or concentration of the at least one analyte from at least one signal of the detection device. In some instances, the testing device also can include at least one evaluation unit having at least one data processing device, such as a microcontroller.

As used herein, "test element receptacle" means a mechanical interface adapted to receive the at least one test element. In some instances, the test element receptacle receives precisely one test element at a time. The mechanical interface may be adapted to at least partially receive the test element and to mechanically secure the test element during measurement. For this purpose, the test element receptacle may include at least one locking element interacting with the test element or parts thereof to at least temporarily retain the test element in a measurement position in which the at least one detection device may detect the at least one analyte-induced change in the test chemistry.

As used herein, "detection device" means an arbitrary element and combination of elements adapted to detect analyte-induced changes in the test chemistry. For this purpose, the detection device may include one or more detectors, such as electrical and/or electrochemical and/or optical detectors. In some instances, the detection device includes one or more photodiodes and/or other photo detectors. Additionally, the detection device may include one or more light sources for illuminating the test field, such as one or more light emitting diodes. Other types of detection devices also are contemplated.

Returning to the test element receptacle of the testing devices, it may include at least one slit into which the test element may be inserted, with a broad edge being a front edge during insertion. The test element receptacle can include at least one abutment surface where the front edge of the test element abuts the abutment surface in a final measurement position in which the at least one detection device may detect the at least one analyte-induced change in the test chemistry of the test field. Thus, as outlined above, the at least two different orientations (i.e., the at least two correct measurement orientations) may include at least one first orientation (i.e., at least one first correct measurement orientation) in which a first edge of a first broad side of the test element is the front edge during insertion, and at least one second orientation (i.e., at least one second correct measurement orientation) in which an opposing second edge of a second, opposing broad side of the test element is the front edge during insertion, where in each of the two orientations preferably one and the same detection device may detect the analyte-induced change in the test chemistry of one and the same test field of the test element.

The testing devices may include one or more interfaces for input and/or output of data, commands and/or operating elements allowing a user to operate one or more functions of the testing device. In some instances, the testing device is a handheld testing device comprising at least one casing, which may easily be carried by a user, such as a testing device having a volume of no more than about 1000 $cm^3$ or of no more than about 500 $cm^3$.

In the test system, the at least one test element and the at least one testing device may be handled separately as long as the test element is not inserted into the testing device, but may interact with each other to qualitatively and/or quantitatively detect the at least one analyte in the body fluid. The test system can be designed so that the test element may be inserted into the test element receptacle in at least two different orientations (i.e., in at least two correct measurement orientations). Therein, the testing device may be adapted, in the at least two different orientations that may also be called correct measurement orientations, to detect an analyte-induced change in the test chemistry of the test field by using the detection device.

The test system also may include at least one positioning element, wherein the positioning element is adapted, in the at least two orientations, to engage at least one positioning aid of the test element inserted into the test element receptacle. In some instances, the at least one positioning element may be a part of the testing device. In other instances, the testing device includes at least two positioning aids, thereby positioning the test field in an essentially identical manner with regard to the detection device in the different orientations.

Besides the at least two different orientations, there may be one or more additional orientations in which the test element may be inserted into the test element receptacle of the testing device, which may be called incorrect orientations, where in this at least one optional incorrect orientation, a detection of the analyte-induced change in the test chemistry of the test field is not detectable.

The positioning element may include one or more positioning elements adapted to mechanically interact with the at least one positioning aid of the test element. Thus, as outlined above, the positioning element may include one or more elements interacting with the at least one positioning aid of the test element in a key-hole-interaction. When the at least one positioning aid of the test element is at least one notch, the positioning element of the testing device may be one or more protrusions mounted elastically and may interlock into the one or more notches of the test element inserted into the test element receptacle in a correct measurement orientation. In case the at least positioning aid of the test element includes one or more cavities and/or holes, the positioning element of the testing device may have one or more bolds movably or elastically mounted that interlock into the at least one cavity and/or hole. Thus, the at least one testing device may comprise one or more positioning elements movably mounted inside the testing device, thereby allowing for the test element to be inserted into the test element receptacle, giving way to the test element, and, when the test element is positioned correctly, to snap into an engagement position engaging the one or more positioning aids of the test element. Similarly, the one or more positioning elements may move for a removal of the test element after use.

The testing device may further include at least one orientation detector such as an optical orientation detector. The orientation detector may fully or partially be identical to the above-mentioned detection device for detecting the analyte-induced change in the test chemistry. In some instances, however, the at least one orientation detector includes at least one separate detector separate from the above-mentioned detection device. The orientation detector may be at least one photo detector and/or at least one light source, such as for detecting the presence of one or more color fields of an orientation indication element of the test element in a field of view of the orientation detector. The orientation detector generally detects at least one orientation indication element of the test element inserted into the test element receptacle, the orientation indication element having a symmetrical shape, in the at least two orientations. Further, the orientation detection may be adapted to detect whether the test element is inserted in an incorrect orientation, such as by the presence and/or absence of the orientation indication element in the field of view of the orientation detector.

The test systems may be a single test strip system. In this single test strip system, only one test element may be inserted into the test element receptacle in a time, preferably manually.

Methods

In view of the test elements and systems above, methods of detecting an analyte are provided herein that incorporate the inventive concept. The methods rely on the test systems as disclosed herein.

In the methods, a user chooses an orientation of the test element, which is inserted into the test element receptacle of the testing device in the chosen orientation. Before or after insertion of the test element, a sample of the body fluid is applied to the test element. At least one analyte-induced change in the test field is detected by the detection device of the testing device, and a concentration of the analyte is derived thereof. Subsequently, the test element may be removed from the test element receptacle. Further, the test element may be disposed of.

EXAMPLES

The inventive concept will be more fully understood upon consideration of the following non-limiting examples, which are offered for purposes of illustration, not limitation.

Figure 1:
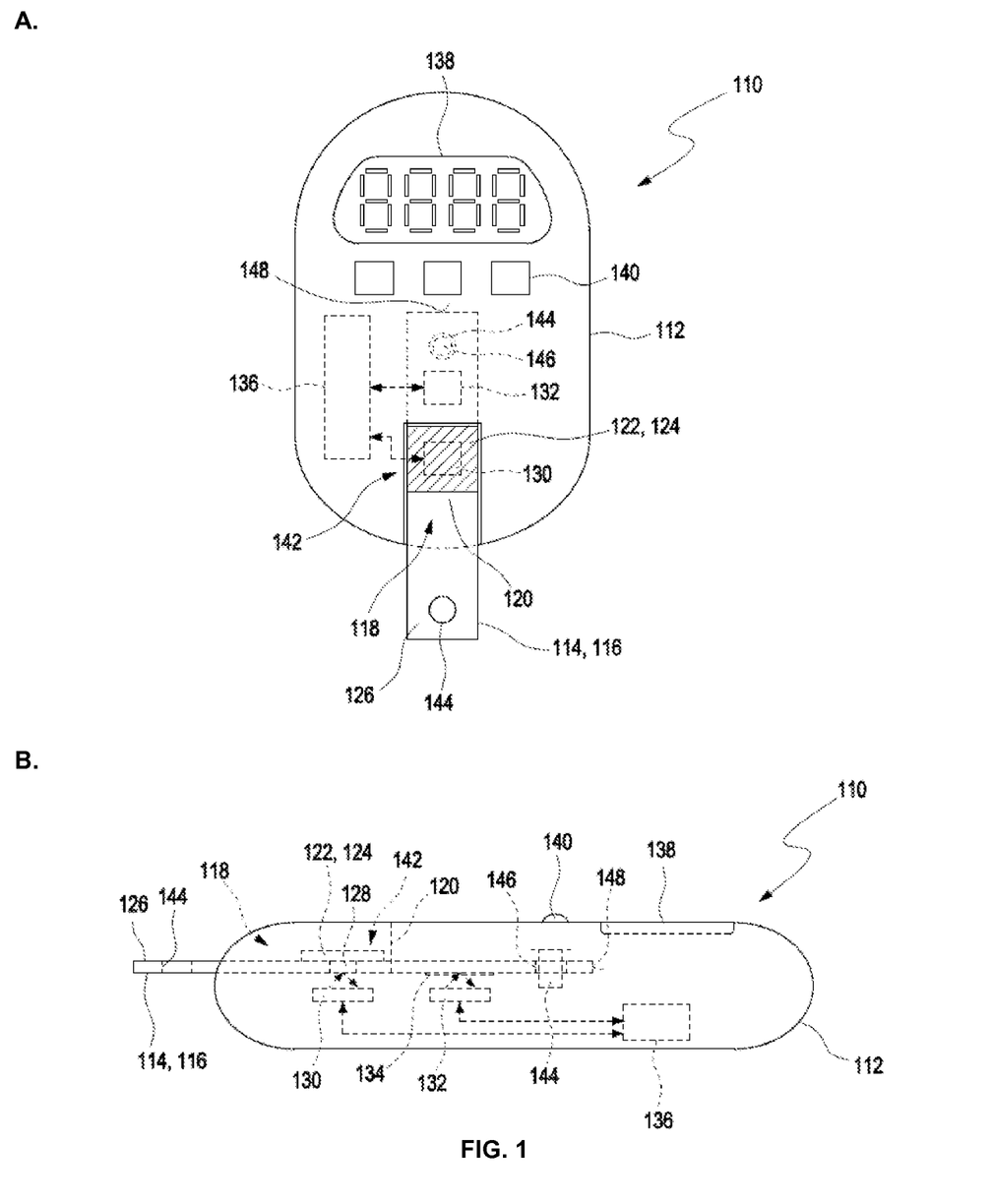

FIGS. 1A-B show an exemplary embodiment of a test system 110. FIG. 1A shows a top view of the test system 110, whereas FIG. 1B shows a cross-sectional view of the test system 110 according to FIG. 1A.

The test system 110 includes a testing device 112, such as a hand-held testing device, and a test element 114. In the embodiment depicted, the test element 114 is designed as a single use test strip 116. The testing device 112 includes a test element receptacle 118 having a slit 120 through which the test element 114 may be manually inserted into the testing device 112.

The test element 114 is a strip-shaped test element 114 or a test strip, which includes a test field 122 having a test chemistry 124. In FIGS. 1A-B, the test field 122 is applied to a top side of a strip-shaped carrier element 126, which may contain a viewing window 128, such as a through-hole (FIG. 1B). Through the viewing window 128, a color change or any other detectable change such as an optically detectable change of the test field 122 and/or the test chemistry 124 contained therein may be detected by a detection device 130 of the testing device 112, such as by one or more optical detectors. Thus, a color change of the test chemistry 124 and/or the test field 122 may be detected by using a reflective mode, as schematically depicted in FIG. 1B.

As further depicted in FIGS. 1A-B, the testing device 112 also may include one or more orientation detectors 132, such as one or more optical orientation detectors 132 for detecting the absence or presence of one or more orientation indication element 134, such as a color field on the backside of the carrier element 126. Further examples will be given below.

The testing device 112 may further include one or more additional components. Thus, the testing device 112, as indicated in FIGS. 1A-B, may contain one or more evaluation devices 136, which may interact with the detection device 130 and/or the orientation detector 132 to detect at least one analyte in a body fluid by using the test element 114. The testing device may further include one or more user interfaces, such as a display 138 and/or one or more operating elements 140, such as push buttons or other types of operating elements.

For qualitatively and/or quantitatively detecting at least one analyte in a sample of the body fluid, the sample of the body fluid, such as a drop of blood from a finger, an earlobe or another body part, is applied to one or more application sites 142 of the test element 114. As shown in FIGS. 1A-B, the application site 142 may be the top surface or application surface of the test field 122. However, as explained in further detail below, other possibilities are contemplated.

The order of the process steps for detecting the analyte in the body fluid may be adapted to the type of application site 142. In the so-called "top dosing" systems as depicted in FIGS. 1A-B, firstly, the sample fluid may be applied to the application site 142 before inserting the test element 114 into the test element receptacle 118. This way of applying the sample of the body fluid also may be called an "outside" mode, since the sample of the body fluid is applied while the test element 114 is still outside the test element receptacle 118. In a so-called "inside" mode, the test element 114 and the testing device 112 may be designed such that the sample of the body fluid may be applied to the test element 114 while the test element 114 is inserted into the test element receptacle 118. Examples of test elements 114 for the inside mode are capillary test elements as explained in detail with respect to FIGS. 4A-B below.

The test element 114 and the testing device 112 also may include one or more elements for positioning the test element 114 inside the test element receptacle 118. Thus, the test element 114 may have one or more positioning aids 144, which may engage one or more positioning elements 146 of the testing device 112. The positioning aids 144 can be located symmetrically with regard to the test field 122. As shown in FIGS. 1A-B, the positioning aid 144 can be through-holes in the carrier element 126, and the positioning element 146 can be at least one pin, which locks into the through-hole close to the front edge 148 of the test element 114 when inserted into the test element receptacle 118. However, other possibilities are contemplated.

The test element 114 as shown in FIGS. 1A-B may be inserted in four different orientations into the test element receptacle 118. Thereof, correct measurement orientations exist as well as incorrect orientations.

Figure 2:
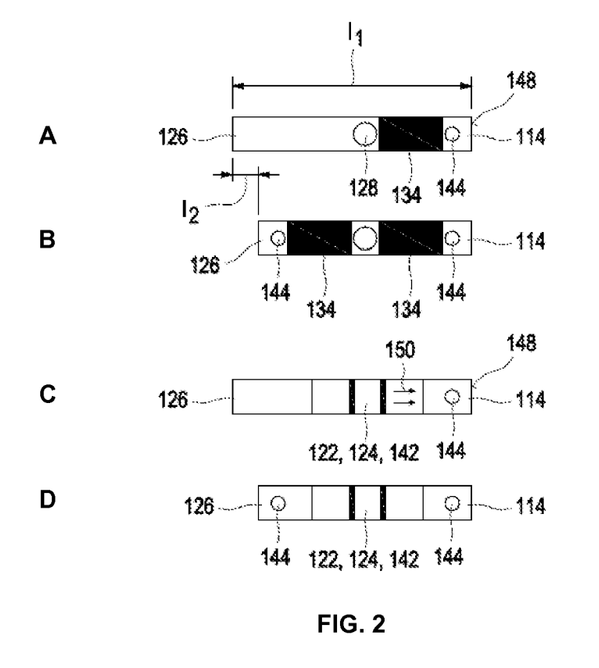
FIGS. 2A and 2C show a backside view and a front view of a test element as known in the art. For comparison.
FIGS. 2B and 2D show a backside view and a frontside view of an exemplary test element as disclosed herein.

FIGS. 2A and 2C show a backside view and a frontside view of a test element 114 as known in the art, which is commercially available under the trade name Accu-Chek® Active. These test elements 114 have a length l1 of about 48 mm and a width of about 6 mm, although other dimensions are possible.

Further, and as outlined above in FIGS. 1A-B, the test elements 114 include a test field 122 with a test chemistry 124, which may optically be monitored via a viewing window 128 in the carrier element 126 from the backside shown in FIG. 2A. The test field 122 may have a length of about 5 mm and a width of about 6 mm.

As shown in FIGS. 2A and 2C, the test element 114 has an asymmetric shape such that the correct measurement orientation in which the test element 114 has to be inserted into the test element receptacle 118 for optical measurement is clearly defined. Thus, the test element 114 has to be inserted with the test field 122 in an upward direction, with the front edge 148 being inserted first. Only in this orientation out of four possible orientations of the test element 114, the detection device 130 may view the test chemistry 124 through the viewing window 128. As shown in FIG. 2A, test elements 114 of the known type further have an orientation indication element 134 on their backside, which may be detected by the orientation detector 132 when the test element 114 is correctly inserted.

In contrast, FIGS. 2B and 2D show a test element 114 according to the present disclosure, in views corresponding to FIGS. 2A and 2C, respectively. As shown in FIG. 2B, the test strip of the test element 114 is shortened on one side by a distance l2, such as by a distance of about 5.9 mm, such that the test field 122 and the viewing window 128 are located symmetrically with the short edges of the test element 114. Generally, the test element 114 may have a rectangular shape. Additionally, the test element 114 may be symmetric with regard to the positioning aids 144, which are positioned symmetrically with regard to the test field 122. Additionally, two orientation indication elements 134 may be provided, as shown in FIG. 2B, symmetrically with regard to the test field 122 and/or the viewing window 128.

By modifying a conventional test element of FIGS. 2A and 2C, a transformation of the test element 114 into a symmetrical test element may be performed. The symmetrical test element 114 as shown in FIGS. 2B and 2D has a mirror symmetry with regard to a mirror plane perpendicular to the plane of view of the figures and perpendicular to the longitudinal side of the rectangle of the test element 114. Thus, out of four possible orientations, the number of correct measurement orientations is doubled when compared to the known test element shown in FIGS. 2A and 2C. That is, the known test element shown in FIGS. 2A and 2C has only one correct measurement orientation, with the front edge 148 being inserted into the slit 120. In the embodiments shown in FIGS.

2B and 2D, the test element 114 may be inserted with the opposing edge, too, as long as the test field 122 is located in an upward direction in FIG. 1B. By doubling the positioning aids 144, again symmetrically with regard to the test field 122, an engagement of the positioning element 146 with the positioning aid 144 in both correct measurement orientation is possible. Thus, modifying known test elements 114 according to the exemplary embodiment of FIGS. 2B and 2D provides a possibility of continuing to use known testing devices 112, such as testing devices of the type Accu-Chek® Active. The modifications imply a shortening of the left side of the test element 114 by a defined distance, such as about 5.9 mm. Additionally, a second positioning aid 144 may be provided on the left side, such as a second through-hole.

Further, a doubling of the orientation indication element 134 may be performed by doubling a color field, specifically a black field. Thereby, both ends of the test element 114 are identical with regard to insertion. In both correct measurement orientations, the viewing window 128 is positioned correctly above the detection device 130. Indicators indicating a correct insertion of the test strip, as shown by reference number 150 in FIG. 2C, may be omitted or alternatively duplicated.

Due to the top dosing system shown in FIGS. 2A-2D, as opposed to capillary systems explained below, this type of test element 114 typically may only be provided in a plane-symmetric or mirror-symmetric way, since, still, the test field 122 has to face in an upward direction as in FIG. 1B. With the test field 122 facing in an upward direction, both ends of the test element 114 are equal with regard to insertion and measurement of the analyte concentration. However, as will be explained in further detail below, other embodiments are possible.

Some test systems 110 known in the art provide a specific outside mode, in which, firstly, the test element 114 is inserted into the test element receptacle 118 for initiating the testing device 112 and for calibrating. Subsequently, the test element 114 is removed from the test element receptacle 118 for applying (top dosing) the sample of the body fluid. Subsequently, the test element 114 with the sample applied to the test field 122 is re-inserted into the test element receptacle 118 for measuring the analyte concentration. In this procedure, such as by using the test system 110 shown in FIGS. 1A-B or in other embodiments, an insertion of the test element 114 into the test element receptacle 118 has to take place twice. Thus, in conventional test elements 114 having an asymmetric shape as shown in FIGS. 2A and 2C, the possibility of choosing an incorrect orientation is increased even more. In the test element 114 as shown in FIGS. 2B and 2D, however, the opposing short edges may be switched between the insertion procedures. Thus, as an example, the right edge in FIGS. 2B and 2C may be inserted into the slit 120 during the first insertion. Then, after removal of the test element 114 from the test element receptacle 118 and after the application of the sample, the left edge in FIGS. 2B and 2D may be inserted into the slit 120 during the second insertion, or vice versa. Still, a correct measurement is possible. Thus, the symmetric shape of the test element 114 in FIGS. 2B and 2D helps to avoid specific errors of the user, such as an incorrect choice of the orientation during insertion.

As shown in FIGS. 2B and 2D, the test element 114 can be shortened when compared to the conventional test element of FIGS. 2A and 2C to obtain the above-mentioned symmetry. Other modifications are possible, however. Thus, as shown in FIGS. 2B and 2D, with the exemplary length given above, the test strip will be shortened by about 12.5%. By shortening the test strip, a reduced handling region on the side opposed to the edge inserted into the slit 120 occurs when compared to the known test element in FIGS. 2A and 2C. This shortening of the test strip may induce problems with regard to the handling of the test strips, specifically when used by elderly persons. Specifically, the portion of the test element 114 extending from the left edge of the testing device 112 in FIG. 1B is shortened. A specific advantage of the embodiment shown in FIGS. 2B and 2D, however, is that the testing device 112 does not have to be modified when compared to the testing device 112 used for the known test elements 114 in FIGS. 2A and 2C.

Other embodiments also are contemplated, which partly may imply a modification of the testing device 112, such as by re-positioning the detection device 130 and/or the orientation detector 132. Further, the positioning of the positioning element 146 inside the testing device 112 may have to be modified. The modifications mentioned above may simply be performed by a redesign of a printed circuit board carrying the detection device 130 and/or the orientation detector 132 and/or by other modifications.

Figure 3:
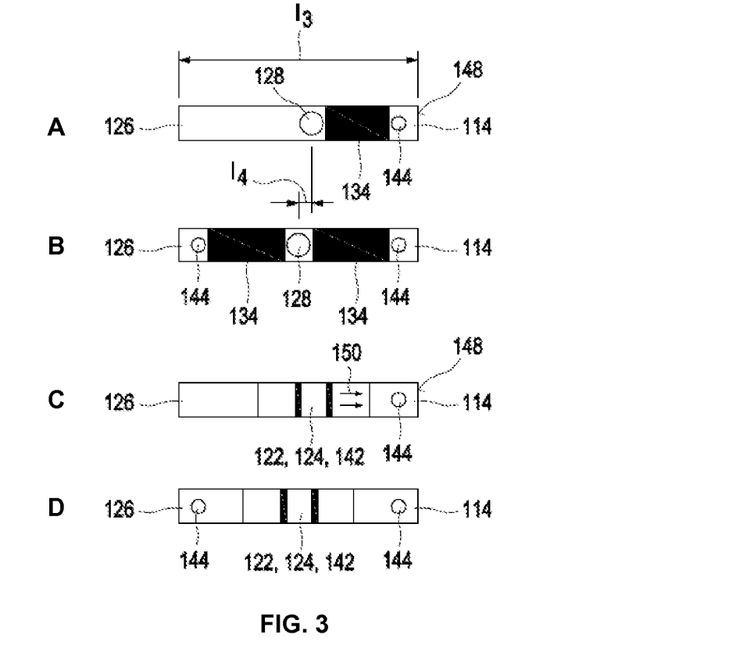
FIGS. 3A and 3C show a backside view of another test element as known in the art. For comparison.
FIGS. 3B and 3D show a backside view and a frontside view of another exemplary test element as disclosed herein.

An exemplary test element 114, in which a shortening of the test element 114 is avoided, is shown in FIGS. 3B and 3D. In FIGS. 3A and 3C, a conventional test element 114 is shown, in an identical view as was shown in FIGS. 2A and 2C. Thus, the length l3 shown in FIG. 3A may be identical to the length l1 in FIG. 2A, such as l3=about 48 mm. For further details of the known test element 114, reference may be made to the description of FIGS. 2A and 2C above.

In FIGS. 3B and 3D, the length of the test element 114 is identical to the known test element shown in FIGS. 3A and 3C. To obtain symmetry, however, the test field 122 and, optionally the viewing window 128 are moved to the left, such as by distance l4, of about 2.95 mm. Again, a second positioning aid 144 may be provided, especially mirror-symmetrically with regard to the test field 122 and/or the viewing window 128, such as by providing a second through-hole as shown in FIGS. 3B and 3D. Again, the orientation indication element 134 may be duplicated as shown in FIG. 3B.

As shown in FIGS. 3B and 3D, the test strip 114 may be inserted into a modified testing device 112. In the modified testing device, as supposed to a testing device used for the known test strip shown in FIGS. 3A and 3C, the detection device 130, the orientation detector 132 and, optionally, the positioning element 146 may be moved. Thus, the detection device 130 in FIG. 1B may have to be moved by distance l4, such as by about 2.95 mm, to the left side.

The exemplary test elements 114 in FIGS. 2B, 2D, 3B and 3D therefore exhibit a mirror-symmetry with regard to a middle plane of the test element 114. Thus, out of four possible orientations, two orientations are correct measurement orientations. By using the inventive concept of the present disclosure, a further degree of symmetry may be provided. Generally, the symmetry in the top dosing system is broken by the asymmetry of the sample application surface of the test field 122, as may be seen in FIG. 1B. However, test elements 114 may be realized, in which analyte-induced change in at least one detectable property of the test chemistry 124 may be detected from both sides.

Figure 4:
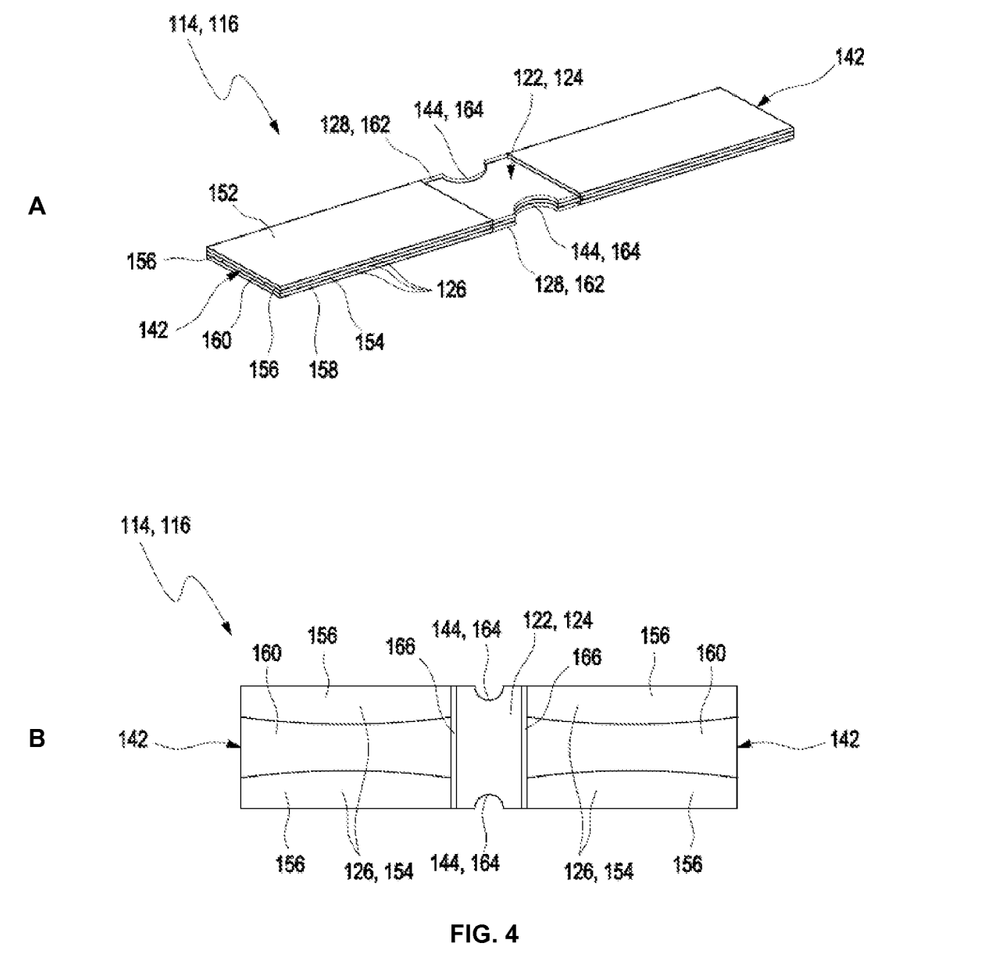
FIGS. 4A-B show different views of the test element of FIGS. 3B and 3D.

An example of an embodiment of a test element 114 that provides such an increased degree of symmetry is shown in FIGS. 4A and 4B. FIG. 4A shows a perspective view of the test element 114, whereas FIG. 4B shows a cross-sectional view of the test element 114 of FIG. 4A through a spacer plane. This test element 114 may be used with the same or a similar testing device 112 as shown in FIGS. 1A-B.

The test element 114 shown in FIGS. 4A-B may be a single-use test strip 116. Here, the test element 114 may include a plurality of carrier elements 126 that form a layer set-up. Thus, in FIGS. 4A-B, the carrier element 126 may include a top layer 152, such as a top foil, a capillary layer 154 between two or more spacer elements 156, and a bottom layer 158, such as a bottom foil. Other configurations are contemplated.

As shown in FIG. 4B, the spacer elements 156 are spaced apart such that in between the spacer element 156 and in between the top layer 152 and the bottom 158, a capillary element 160 is provided, such as a capillary channel. As shown in FIGS. 4A-B, two capillary channels can be provided, one leading from the left edge to the middle and one leading from the right edge to the middle. Thus, the test element 114 provides two application sites 142 for sample application (i.e., the capillary openings of the capillary elements 160).

A test field 122 having a test chemistry 124 can be provided in the middle of the test element 114. The test field 122 may be imbedded in between two transparent elements 162, which may form viewing windows 128 through which an analyte-induced change in the test chemistry 124 may be observed by the detection device 130. The transparent elements 162 may be formed by transparent carrier foils, which directly or indirectly may be applied to the test chemistry 124 of vice versa.

As above, the test element 114 shown in FIGS. 4A-B provides symmetry. Thus, the test field 122 is positioned in the middle of the test strip, as can be seen in FIG. 4B. FIG. 4B further shows that a plane-symmetry is provided with regard to a mirror plane perpendicular to the plane of view. However, in addition, a plane symmetry with regard to the plane of view in FIG. 4B is provided since the analyte-induced change in the test chemistry 124 may be detected both from the upper side in FIG. 4A and from the lower side. Thus, the test element 114 in FIGS. 4A-B provides a mirror symmetry with regard to two perpendicular mirror planes.

In addition, and as shown in FIGS. 2B, 2D, 3B and 3D, the test element 114 may provide one or more positioning aids 144. Since positioning aids 144 formed by through-holes are disadvantageous with regard to the capillary elements 160, the test element 114 may include two or more notches 164, which are symmetrical with regard to the test field 122. The testing device 112 may provide corresponding hooks or catches, which engage the notches 164.

In use, the test element 114 shown in FIGS. 4A-B may be inserted in all four possible orientations, all of which are correct measurement orientations, into the slit 120 of the test element receptacle 118. After insertion, the sample of the body fluid may be applied to the application site 142, formed by the opening of the capillary element 160 protruding from testing device 112. After sample application, such as after application of a drop of blood, the sample flows through the capillary element 160 to the centrally located test field 122 having the at least one test chemistry 124. The opposing capillary element 160 may function as a "sink" for access sample. In between the test field 122 and the capillary elements 160, an intermediate space 166 (see, FIG. 4B) may be provided.

One or more test fields 122 having one or more test chemistries 124 may be provided. Thus, as shown in FIG. 4B, the test chemistry 124 may extend from the top layer 152 to the bottom layer 158. However, test fields 122 may be provided on both sides of the capillary layer 154 and/or the spacer elements 156. As such, the spacer elements 156 may be covered, on both sides, by test elements 114, each having a test chemistry 124. In the latter case, the sample may react with both test fields 122 on both sides of the capillary element 160 such that the analyte-induced change in the at least one detectable property of the test chemistry 124 may be detected from both sides through the viewing windows 128. The test chemistry 124 may be provided from the same manufacturing lot and, thus, a similar or identical behavior with regard to the analyte-induced change may be guaranteed.

By using these features, a full symmetry of the test element 114 may be provided. Thus, the test element 114 may be inserted into the test element receptacle 118 in all four possible correct measurement orientations and, still, the test system 110 may function properly. An error induced by a wrong choice of the orientation by the user is prevented. In this case, all measures inside the testing device 112, which are typically used for preventing a false orientation may be omitted, and the testing device 112 may significantly be simplified.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

| Listing of reference numbers: | |
|---|---|
| 110 | Test system |
| 112 | Testing device |
| 114 | Test element |
| 116 | single-use test strip |
| 118 | test element receptacle |
| 120 | slit |
| 122 | test field |
| 124 | test chemistry |
| 126 | carrier element |
| 128 | viewing window |
| 130 | detection device |
| 132 | orientation detector |
| 134 | orientation indication element |
| 136 | evaluation device |
| 138 | display |
| 140 | operating element |
| 142 | application site |
| 144 | positioning aid |
| 146 | positioning element |
| 148 | front edge |
| 150 | indicators |
| 152 | top layer |
| 154 | capillary layer |
| 156 | spacer element |
| 158 | bottom layer |
| 160 | capillary element |
| 162 | transparent element |
| 164 | notch |
| 166 | intermediate space |

The invention claimed is:

1. A test element for detecting at least one analyte in a body fluid sample, the test element comprising:
at least one strip-shaped carrier element; and
at least one test field having at least one test chemistry for detecting the at least one analyte,
wherein the test element has a symmetrical shape so that the test element may be inserted in at least two different correct measurement orientations into a test element receptacle of a testing device having a detection device, wherein in the at least two different correct measurement orientations at least one analyte-induced change in the test chemistry of the test field is detectable, and wherein the test element has a symmetry selected from the group consisting of a mirror symmetry about a virtual middle plane of the test element and a symmetry with respect to a virtual line or axis.

2. The test element of claim 1, wherein the test element is a single use test strip designed to be used only once for detecting the at least one analyte in the body fluid sample.

3. The test element of claim 1, wherein the analyte-induced change in the test chemistry is an optical change that can be detected by the detection device.

4. The test element of claim 1, wherein the symmetry is the mirror symmetry about the virtual middle plane of the test element, and wherein the virtual middle plane of the test element is a middle plane perpendicular to a plane of the strip-shaped carrier element.

5. The test element of claim 1, wherein the symmetry is the symmetry with respect to the virtual line or axis, and wherein the axis is a symmetry axis centrally penetrating the test element.

6. The test element of claim 1, wherein the test element has a two-fold symmetry or four-fold symmetry.

7. The test element of claim 1 further comprising at least one mechanical positioning aid, wherein the at least one mechanical positioning aid engages, in the at least two correct measurement orientations, at least one positioning element of the testing device to position the test field in all orientations in a substantially identical position with regard to the detection device.

8. The test element of claim 7, wherein the at least one mechanical positioning aid is selected from the group consisting of at least one notch positioned at a longitudinal side of the carrier element; at least one cavity or hole in the carrier element; and at least one catch profile adapted to engage at least one catch element of the positioning element.

9. The test element of claim 1 further comprising at least one orientation indication element having a symmetrical shape, the at least one orientation indication element detectable by at least one orientation detector of the testing device when the test element is inserted into the test element receptacle in the orientations.

10. The test element of claim 1 further comprising at least two sample application sites located symmetrically with regard to the at least one test field.

11. The test element of claim 1 further comprising at least two capillary elements located symmetrically with regard to the at least one test field, wherein the capillary elements convey the body fluid sample from at least one opening of each capillary element to the at least one test field.

12. The test element of claim 1, wherein the at least one test field comprises at least two viewing windows on opposing sides of the test element for detecting an optical change of the test chemistry.

13. A test system for detecting at least one analyte in a body fluid sample, the test system comprising:
at one test element of claim 1; and
a testing device comprising a test element receptacle and a detection device,
wherein the at least one test element may be inserted into the test element receptacle in at least two different correct measurement orientations, and wherein the testing device detects an analyte-induced change in the test chemistry of the test field by using the detection device.

14. The test system of claim 13 further comprising at least one mechanical positioning aid on the at least one test element, wherein the at least one mechanical positioning aid engages, in the at least two different correct measurement orientations, at least one positioning element of the testing device to position the test field in all orientations in a substantially identical position with regard to the detection device.

15. The test system of claim 13, wherein the testing device further comprises at least one orientation detector to detect at least one orientation indication element of the test element inserted into the test element receptacle, the at least one orientation indication element having a symmetrical shape in the at least two orientations.

16. The test system of claim 15, wherein the at least one orientation detector is an optical orientation detector.

17. A method of detecting an analyte in a body fluid sample, the method comprising the steps of:
providing the test system of claim 13;
inserting the test element in a user-selected orientation into the test element receptacle of the test device, wherein before or after inserting the test element the body fluid sample is applied to the test element;
detecting at least one analyte-induced change in the test chemistry of the test field by the detection device; and
providing a concentration of the analyte derived from the at least one analyte-induced change in the test field.

18. The method of claim 17, wherein the analyte-induced change in the test chemistry is one or both of a color change or a change in a remission.

19. The method of claim 17, wherein the analyte is glucose.

* * * * *